US012773463B2

(12) United States Patent
Lautt

(10) Patent No.: US 12,773,463 B2
(45) Date of Patent: Oct. 27, 2026

(54) TEST MEAL, TEST MEAL PACKAGING, METHOD AND USES THEREOF

(71) Applicant: SciMar Ltd., Dauphin (CA)

(72) Inventor: Wayne W. Lautt, Gibsons (CA)

(73) Assignee: SciMar Ltd., Dauphin (CA)

( * ) Notice: Subject to any disclaimer, the term of this patent is extended or adjusted under 35 U.S.C. 154(b) by 666 days.

(21) Appl. No.: 18/006,532

(22) PCT Filed: Jul. 23, 2021

(86) PCT No.: PCT/CA2021/051030
§ 371 (c)(1),
(2) Date: Jan. 23, 2023

(87) PCT Pub. No.: WO2022/016290
PCT Pub. Date: Jan. 27, 2022

(65) Prior Publication Data

US 2023/0256118 A1 Aug. 17, 2023

Related U.S. Application Data

(60) Provisional application No. 63/055,717, filed on Jul. 23, 2020.

(51) Int. Cl.
*A61K 49/00* (2006.01)
*A23L 33/12* (2016.01)
*A23L 33/125* (2016.01)
*A23L 33/185* (2016.01)

(52) U.S. Cl.
CPC .......... *A61K 49/0004* (2013.01); *A23L 33/12* (2016.08); *A23L 33/125* (2016.08); *A23L 33/185* (2016.08)

(58) Field of Classification Search
None
See application file for complete search history.

(56) References Cited

U.S. PATENT DOCUMENTS

2007/0009438 A1* 1/2007 Lautt .................. A61K 49/0004 424/9.1
2013/0219987 A1* 8/2013 Hageman ............... G01N 33/49 73/23.3
2014/0342981 A1 11/2014 Lautt et al.
2019/0216125 A1* 7/2019 Binks ........................ A23L 2/39

FOREIGN PATENT DOCUMENTS

CN 102791148 A1 11/2012
CN 106901337 A 6/2017
CN 210417532 U 4/2020
EP 1660889 B1 5/2011
EP 2544557 B1 2/2018
WO 97/02050 1/1997
WO 2005/017532 A1 2/2005
WO 2005/019833 A1 3/2005
WO 2011/112091 A1 9/2011

OTHER PUBLICATIONS

International Search Report and Written Opinion dated Oct. 20, 2021 relating to PCT/CA2021/051030, 12 pages.
Vannan, Danielle T. et al., Comparison of Glucose and Satiety Hormone Response to Oral Glucose vs. Two Mixed-Nutrient Meals in Rats, Frontiers In Nutrition, Article 89, vol. 5 (Sep. 2018) pp. 1-6.
Wolever, et al., "Variation of postprandial plasma glucose, palatability, and symptoms associated with a standardized mixed test meal versus 75 g oral glucose", Diabetes Care, American Diabetes Association, Alexandria, VA, U.S., vol. 21, No. 3, Mar. 1, 1998 (Mar. 1, 1998), pp. 336-340, XP002482173, ISSN: 0149-5992, DOI: 10.2337/DIACARE.21.3.336, http://dx.doi.org/10.2337/diacare.21.3.336.
Database GNPD [Online] MINTEL; Apr. 30, 2014 (Apr. 30, 2014), anonymous: "Peanut Flavoured Compressed Biscuits", XP093181801, Database accession No. 2396319.
Ode, Katie Larson et al: "Oral glucose tolerance testing in children with cystic fibrosis", Pediatric diabetes, Jun. 1, 2012 (Jun. 1, 2012), pp. 487-492, XP093181981, DOI: 10.1111/j.1399-5448.2009.00632.x, Retrieved from the Internet: URL:https://www.racgp.org.au/getattachment/ef9d5d0a-931 d-42d4-b6b4-9c9344f5a581/Oral-glucose-tolerance-testing.aspx.
First Office Action, Chinese Application No. 202180058292.2, Aug. 22, 2024, 15 pages, machine translation only.
Second Office Action, Chinese Application No. 202180058292.2, Apr. 19, 2025, 22 pages, machine translation only.
European Search Report, European Application No. 21845781, dated Apr. 1, 2025, 15 pages.

* cited by examiner

*Primary Examiner* — Celeste A Roney
(74) *Attorney, Agent, or Firm* — Stinson LLP

(57) ABSTRACT

The present invention provides a test meal composition, a test meal packaging, a test meal kit, and methods and uses of same for detection of prediabetes in an individual. The test meal composition comprises dextrose, lecithin, and soy protein. Additionally, the test meal composition is packaged for consumption by an individual based on a body weight of the individual. The consumption of the test meal is used in methods for detection of prediabetes, and the determination of efficacy of diabetes treatments. Assessment of the presence and degree of prediabetes and diabetes is based on the degree of meal-induced hyperglycemia and hyperinsulinemia.

13 Claims, 7 Drawing Sheets

TEST MEAL, TEST MEAL PACKAGING, METHOD AND USES THEREOF

CROSS-REFERENCE TO RELATED APPLICATION

This patent application claims the benefit of U.S. Provisional Patent Application No. 63/055,717, filed Jul. 23, 2020 which is incorporated by reference in its entirety herein.

FIELD OF INVENTION

The present invention relates generally to a test meal, test meal packaging, and their use in diagnosing hyperglycemia, insulin resistance, Absence of Meal-Induced Insulin Sensitization (AMIS) syndrome, pre-diabetes, and diabetes.

BACKGROUND

AMIS syndrome describes a cluster of related pathologies that include obesity, diabetes, cardiovascular disease, retinal and kidney failure, and the metabolic dysfunctions associated with the originally-named Syndrome X. The original name of the syndrome and the subsequent 13 attempts to rename it, including the American Diabetes Association's renaming as Cardiometabolic Risk (CMR) (Grundy et al., 2005), did not determine a mechanistic link between the pathologies, other than as risk factors for other of the pathologies.

The suggestion to refer to this cluster of pathologies as the AMIS syndrome is based on the discovery of the phenomenon and mechanism of Meal-induced Insulin Sensitization (MIS), and how Absence of Meal-induced Insulin Sensitization (AMIS) results in the initiation of a progressive, predictable cluster of pathologies that are not diagnosed until well into the AMIS syndrome.

MIS is demonstrated by a much larger hypoglycemic response to insulin after a meal as compared with the response to insulin in the fasted state, as first reported in 2001 by the present inventor in rats (Lautt et al., 2001) and later confirmed by the present inventor in humans (Patarrao et al., 2008).

The degree of MIS is determined by the ability of pulses of insulin to cause the secretion of Hepatic Insulin Sensitizing Substance (HISS) from the liver. Normally, a mixed meal activates a hepatic parasympathetic reflex that releases acetylcholine to react with muscarinic receptors in the liver. In the presence of this permissive signal, pulses of insulin stimulate the release of HISS from the liver, which can be eliminated by administration of a muscarinic receptor antagonist.

HISS is released from the liver in response to pulses of insulin, but only in the presence of 2 synergistic, permissive feeding signals, one neural via the hepatic parasympathetic nerves and one chemical through elevation of hepatic glutathione levels (Lautt et al., 2011). The nerve response is mediated by nitric oxide and cGMP. The feeding signals are activated by the presence of food in the upper GI tract, even if the food is a liquid injected into the stomach of anesthetized rats (Sadri et al., 2006). Regular solid rat chow or an intragastric injection of a mixed liquid meal fully activates MIS. However, there is a need to determine the meal components necessary to activate the feeding signals, and thus MIS, in humans.

The lack, or low levels, of HISS in an individual after an insulin pulse is injected is understood to result in a lower degree of MIS or, conversely, a higher degree of AMIS. As noted above, a higher degree of AMIS has been found to result in the initiation of a progressive, predictable cluster of pathologies that include obesity, diabetes, cardiovascular disease, retinal and kidney failure, and the metabolic dysfunctions.

The standard tests used to diagnose Glucose Intolerance in humans generally include: Fasting Plasma Glucose (FPG), Two-Hour Oral Glucose Tolerance Test (OGTT), Hyperinsulinemic-Euglycemic Clamp (HIEC), Homeostatic Measurement Assessment Insulin Resistance (HOMA-IR) and Glycated Hemoglobin (HbA1C). Critical to the current understanding, however, was the demonstration that HISS action cannot be detected by any of these standard tests for Glucose Intolerance (Patarrao et al., 2008; Sadri et al., 2006), thereby accounting for its unknown etiology. Accordingly, there is a need for the development of new technological advancements for the detection if HISS, and consequently, its indication of prediabetes and prediabetes-related pathologies.

SUMMARY OF THE INVENTION

In one aspect, the present invention teaches a test meal composition for consumption by an individual based on the body weight of the individual for detection of prediabetes, the test meal composition comprising dextrose, lecithin, and soy protein.

In another aspect, the present invention teaches a test meal packaging for consumption by an individual based on the body weight of the individual for detection of prediabetes, the test meal packaging comprising: one or more first packets, each first packet containing a first amount of a test meal for consumption, the first amount corresponding to the first body weight unit; the number of first packets (P1) being the body weight of the individual (BW) divided by the first body weight unit (W1) rounded down to the nearest integer.

In another aspect, the present invention teaches a test meal packaging for consumption by an individual based on the body weight of the individual for detection of prediabetes, the test meal packaging comprising: multiple first packets, each first packet containing a first amount of a test meal for consumption, the first amount corresponding to a first body weight unit; and multiple second packets, each second packet containing a second amount of the test meal, the second amount corresponding to a second body weight unit ($W_2$), that is smaller than the first body weight unit; wherein the number of first and second packets of test meal to be consumed by the individual collectively corresponds to a total amount of test meal that is proportional to a body weight of the individual.

In another aspect, the present invention teaches a test meal kit for consumption of test meal by an individual for detection of prediabetes in the individual, the test meal kit comprising: one or more first packets, each first packet containing a first amount of a test meal, the first amount corresponding to a first body weight unit; one or more second packets, each second packet containing a second amount of the test meal, the second amount corresponding to a second body weight unit, the second body weight unit being smaller than the first body weight unit; and a packet scale indicating a number of the first packets and a number of the second packets the individual is to consume based on the body weight of the individual.

In another aspect, the present invention teaches a method of using test meal in the detection of prediabetes in an individual, the method comprising: determining a body weight of the individual; determining an amount of the test meal to be consumed by the individual, the amount corresponding to the body weight of the individual; and consuming the amount of test meal by the individual.

In another aspect, the present invention teaches a use of an amount of test meal for consumption by an individual for detection of prediabetes in the individual, the amount of test meal being proportional to a body weight of the individual.

In another aspect, the present invention teaches a method of diagnosing prediabetes in an individual, the method comprising: fasting the individual for a period of time to produce a fasted individual; measuring a fasted insulin level and a fasted glucose level of the fasted individual; feeding the individual an amount of test meal to produce a fed individual; measuring a fed insulin level and a fed glucose level of the fed individual; calculating a meal induced insulinemia and glycemia (MIG) score by determining the differential between the insulin level and the glucose level of the fed individual and the insulin level and glucose level of the fasted individual; wherein the MIG score indicates the degree of Meal-induced Insulin Sensitization (MIS) in the individual.

In another aspect, the present invention teaches a method of determining efficacy of a diabetes treatment, the method comprising: performing the diagnostic method of diagnosing prediabetes in an individual to produce a first MIG score; administering the diabetes treatment; performing the diagnostic method of diagnosing prediabetes in an individual to produce a second MIG score; comparing the first MIG score with the second MIG score; wherein the second MIG score being lower than the first MIG score indicating efficacy of the diabetes treatment.

In another aspect, the present invention teaches a method of determining efficacy of a diabetes lifestyle intervention, the method comprising: performing the diagnostic method of diagnosing prediabetes in an individual to produce a first MIG score; administering the diabetes lifestyle intervention; performing the diagnostic method of diagnosing prediabetes in an individual to produce a second MIG score; comparing the first MIG score with the second MIG score; wherein the second MIG score being lower than the first MIG score indicating efficacy of the diabetes lifestyle intervention.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Throughout the following description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Test Meal Composition

The inventor has found that test meals of only amino acids, lipids, or glucose fail to activate Meal-induced Insulin Sensitization (MIS), but that a mixture consisting of amino acids, lipids and glucose was effective in activating MIS in humans (Afonso et al. 2016).

Since it is generally difficult to control the rate of consumption and metabolic processing of solid meals, a liquid test meal can avoid such issues. Thus, a reconstituted powdered meal has been formulated. The present test meal is a blend of carbohydrate, lipid, and protein (soymilk powder), which has been found to activate the necessary feeding signals to activate MIS, and glucose has been added to magnify the response. The product is a powder to be dosed according to body weight to help assess the individual's ability to release HISS, and thus, help to detect prediabetes.

Thus, according to one example embodiment, a test meal composition for consumption by an individual for detection of prediabetes is provided, where the test meal composition comprises dextrose, lecithin, and soy protein.

Dextrose is a simple sugar that is made from corn and corresponds to glucose, or blood sugar. Since dextrose is a simple sugar, it can raise the individual's blood sugar level very quickly upon consumption. In one aspect, the present invention provides a test meal composition comprising 80-85% by weight of dextrose. In a preferred embodiment, the amount of dextrose in the test meal composition is 82.5% by weight.

Lecithin is a fat that is essential to the cells of the body. It is typically found in many foods, including soybeans and egg yolks. In one aspect, the present invention provides a test meal composition comprising 2-8% by weight of lecithin. In a preferred embodiment, the amount of lecithin in the test meal composition is 5% by weight.

Soy protein is a protein that is, unsurprisingly, isolated from soybean. It is made from soybean meal that has been dehulled and defatted. A range of proportions of compositions would all work. The source of protein and fat is also able to be widely varied and still work. In one aspect, the present invention provides a test meal composition comprising 10-15% by weight of soy protein. In a preferred embodiment, the amount of soy protein in the test meal composition is 12.5% by weight.

Thus, in the present embodiment, the test meal composition comprises 82.5% dextrose, 5% lecithin, and 12.5% soy protein blended together in powdered form.

Test Meal Packaging

Figure 1:
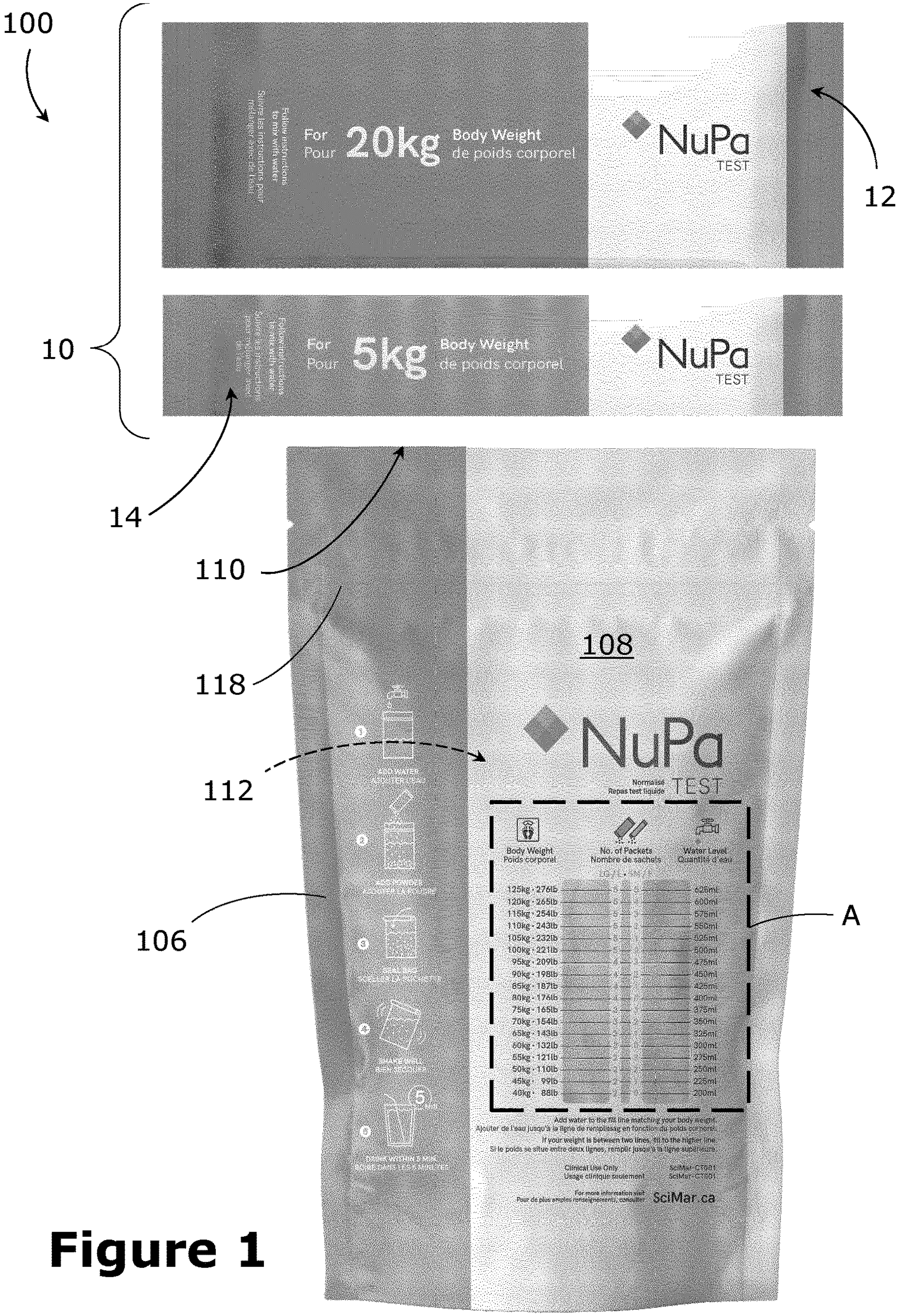
FIG. 1 is a meal test package for a meal test kit according to an embodiment of the present invention.

To remove the "measuring" step required when portioning out the necessary amount of the test meal to be consumed by the individual, the present invention provides a test meal packaging with 10 pre-portioned packets of the test meal. An embodiment of a test meal packaging (10) for consumption by an individual is illustrated in FIG. 1. As noted above, the amount of test meal to be consumed by the individual is based on the body weight of the individual, and is used to help assess the individual's ability to release HISS, and thus, the detection of prediabetes.

Test meal packaging (10) includes one or more first packets 12, each first packet (12) containing a first amount of a test meal for consumption, where the first amount corresponds to a first body weight unit. In the present embodiment, the first amount is one thousandth of the first body weight unit and the first body weight unit is 20 kg. Thus, as depicted, since the first body weight unit is 20 kg, the first amount of the test meal in first packet (12) is correspondingly 20 g of the test meal. As understood by the skilled person, the first body weight unit may be a different number, such as 10 kg or 25 kg.

While only one first packet (12) is shown, test meal packaging (10) may include multiple first packets 12. In one embodiment, the number of first packets ($P_1$) included in test meal packaging (10) may be calculated using the formula:

$$P_1=BW/W_1$$

where BW is the body weight of the individual, $W_1$ is the first body weight unit, and $P_1$ is rounded down to the nearest integer.

For example, if BW of the individual is 40 kg and $W_1$ is 20 kg, $P_1$ equals 2. Thus, two first packets 12, for a total of 40 g of test meal, may be included in test meal packaging (10) for consumption by the individual with a body weight of 40 kg. In another example, if BW of the individual is 72 kg and $W_1$ is 20 kg, $P_1$ equals 3 (3.6 rounded down to 3). Thus, three first packets 12, for a total of 60 g of test meal, may be included in test meal packaging (10) for consumption by an individual with a body weight of 72 kg.

To at least partially account for the rounding down, test meal packaging (10) may additionally include one or more second packets 14, where each second packet (14) contains a second amount of the test meal. The second amount corresponds to a second body weight unit ($W_2$), which is smaller than the first body weight unit ($W_1$).

In the present embodiment, the second amount is also one thousandth of the second body weight unit, and the second body weight unit is a quarter of the first body weight unit. Thus, as depicted, the second body weight unit is 5 kg, and the second amount of the test meal in second packet (14) is correspondingly 5 grams of the test meal. As understood by the skilled person, the second body weight unit may be a different number, such as 2 kg or 1 kg.

While only one second packet (14) is shown, test meal packaging (10) may include multiple second packets 14. In one embodiment, the number of second packets ($P_2$) included in test meal packaging (10) may be calculated using the formula:

$$P_2=(BW-P_1*W_1)/W_2$$

where BW is the body weight of the individual, $P_1$ is the number of first packets 12 included in test meal packaging (10), $W_2$ is the second body weight unit, and $P_2$ is rounded down to the nearest integer.

Continuing the above example, if BW of the individual is 72 kg, $W_1$ is kg, $P_1$ is 3, and $W_2$ is 5 kg, $P_2$ equals 2 (2.4 rounded down to 2). Thus, three first packets 12 (with 20 g/packet) and two second packets 14 (with 5 g/packet), for a total of 70 g of test meal, may be included in test meal packaging (10) for consumption by an individual with a body weight of 72 kg.

In other applications, the number of pre-portioned first and second packets 12, 14 in test meal packaging (10) may not be customized to correspond to the individual's body weight. In such cases, test meal packaging (10) may simply include multiple first packets 12 and multiple second packets 14. The individual is then responsible to determine the number of both first and second packets 12, 14 he or she is to consume so that they collectively correspond to a total amount of test meal that is proportional to the body weight of the individual.

As before, the first amount may be one thousandth of the first body weight unit, the first body weight unit may be 20 kg, and the first amount of the test meal in first packet (12) may correspondingly be 20 g of the test meal. As understood by the skilled person, the first body weight unit may be a different number, such as 10 kg or 25 kg, or some other amount. A different measurement system, such as pounds may be used.

The second amount may also be one thousandth of the second body weight unit, and the second body weight unit may be a quarter of the first body weight unit. Thus, the second body weight unit may be 5 kg, and the second amount of the test meal in second packet (14) may correspondingly be 5 grams of the test meal. As understood by the skilled person, the second body weight unit may be a different number, such as 2 kg or 1 kg, or some other amount. A different measurement system, such as pounds may be used.

A preferred test meal in test meal packaging (10) may be the test meal composition described above, including dextrose, lecithin, and soy protein. In the present embodiment, the test meal comprises 82.5% by weight of dextrose, 5% by weight of lecithin, and 12.5% by weight of soy protein in powdered form. In other embodiments, other test meals may be used.

Test Meal Kit

Figure 2:
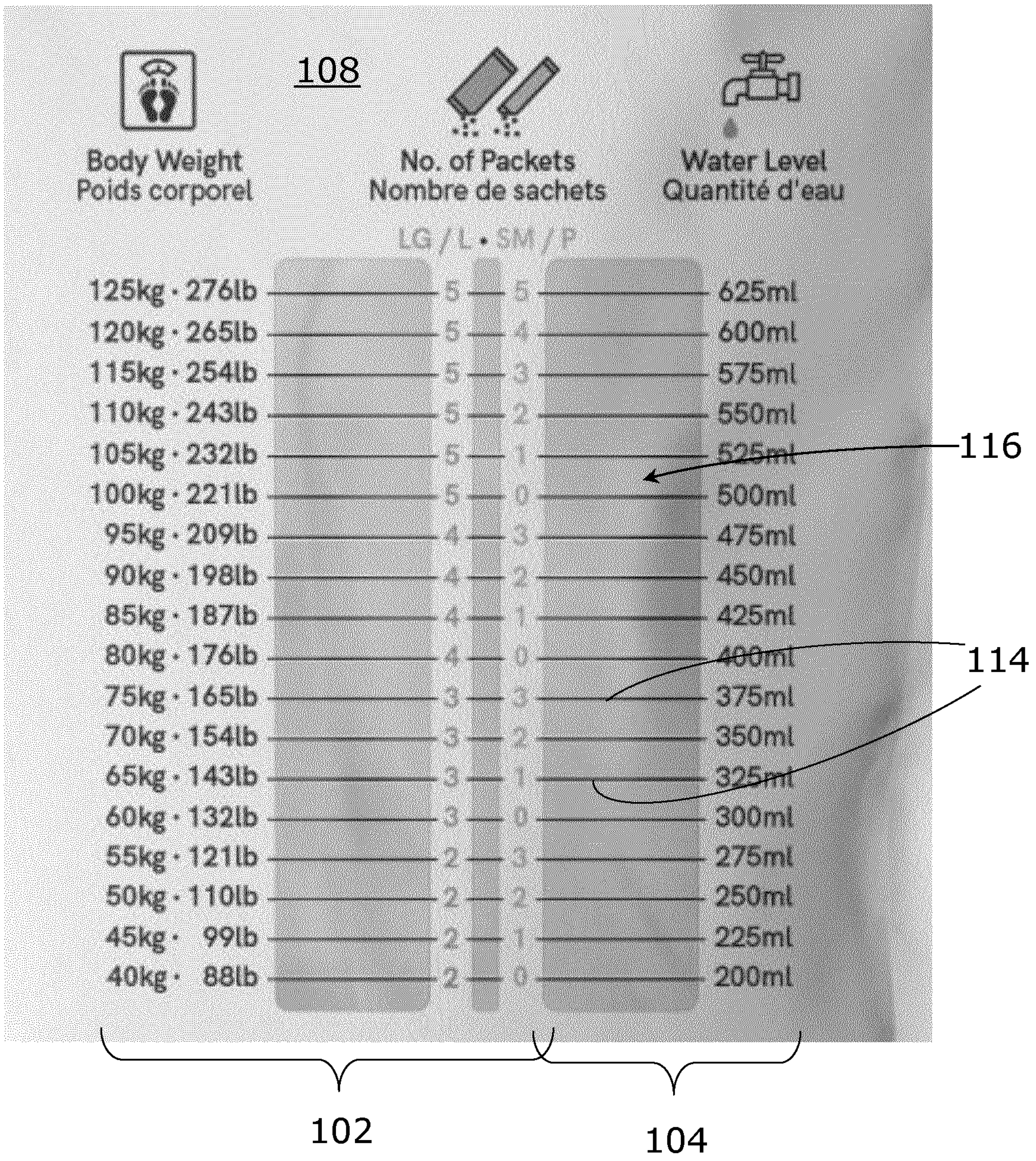
FIG. 2 is an enlarged view of portion A of FIG. 1.

In some applications, test meal packaging (10) may form part of test meal kit (100), see FIGS. 1 and 2. In addition to test meal packaging (10) discussed above, test meal kit (100) may further include a packet scale (102), which indicates a number of first packets 12 and a number of second packets 14 the individual is to consume based on the body weight of the individual. As discussed above, the number of first and second packets 12, 14 indicated by packet scale (102) collectively correspond to a total amount of test meal that is proportional to a body weight of the individual.

For example, $P_1=BW/W_1$, rounded down to the nearest integer, and $P_2=(BW-P_1*W_1)/W_2$, rounded down to the nearest integer. In such a case, for an individual with a body weight of 65 kg, packet scale (102) would indicate that the individual should consume three first packets 12 and one second packet (14), for a total amount of test meal of 65 g.

Test meal kit (100) may further include a water scale (104) that indicates a corresponding volume of water that is to be mixed with the test meal from the number of first packets 12 and the number of second packets 14. In the present embodiment, the volume of water is proportional to the amount of test meal and proportional to the body weight of the individual. In particular, the volume of water may be 5 mL of water for every gram of the amount of test meal used. For example, the individual with a body weight of 65 kg would require 65 g of test meal, and water scale (104) would further indicate that the 65 g of test meal is to be mixed with 325 mL of water.

In the shown embodiment, test meal kit (100) further includes a pouch (106) with an external surface (108) and an opening (110) through which an internal space (112), defined therein, may be accessed. Internal space (112) is where the water and the total amount of test meal to be consumed by the individual may be mixed.

Moreover, as shown, packet scale (102) and water scale (104) are printed on external surface (108) of pouch (106). In other applications, packet scale (102) and water scale (104) may be conveyed to the individual on separate printed or digital instruction items. The content of the present example packet scale (102) and water scale (104) is reproduced below:

| | Package Size | | |
|---|---|---|---|
| Body Weight (kg) | 5 g Pkg | 20 g Pkg | Water (mL) |
| 40 | 0 | 2 | 200 |
| 45 | 1 | 2 | 225 |
| 50 | 2 | 2 | 250 |
| 55 | 3 | 2 | 275 |
| 60 | 0 | 3 | 300 |
| 65 | 1 | 3 | 325 |
| 70 | 2 | 3 | 350 |
| 75 | 3 | 3 | 375 |
| 80 | 0 | 4 | 400 |
| 85 | 1 | 4 | 425 |
| 90 | 2 | 4 | 450 |
| 95 | 3 | 4 | 475 |
| 100 | 0 | 5 | 500 |

As best seen in FIG. 2, water scale (102) further includes measurement markers 114 on external surface (108) of pouch (106). Measurement markers 114 are presently shown to be fill lines that indicate the level of water within internal space (112) that is to be filled for mixing with the test meal. Pouch (106) is dimensioned such that the volume of internal space (112) corresponds with the water measurement markers 114.

In that regard, pouch (106) may further include transparent or translucent windows (116) that are positioned proximate, or over which, measurement markers 114 extend. Windows (116) would help allow the user to view internal space (112) from outside pouch (106). As such, when filling pouch (106) with water, the user may visually assess the level to which water has reached within internal space (112), to ensure the water has reached the correct measurement marker (114).

Optionally, pouch (106) may include a resealable seal (118) secured proximate opening (110). Resealable seal (118) helps to fluidly seal pouch (106) for mixing of the test meal and the water when pouch (106) is shaken.

Method and Use of Test Meal

Figure 3:
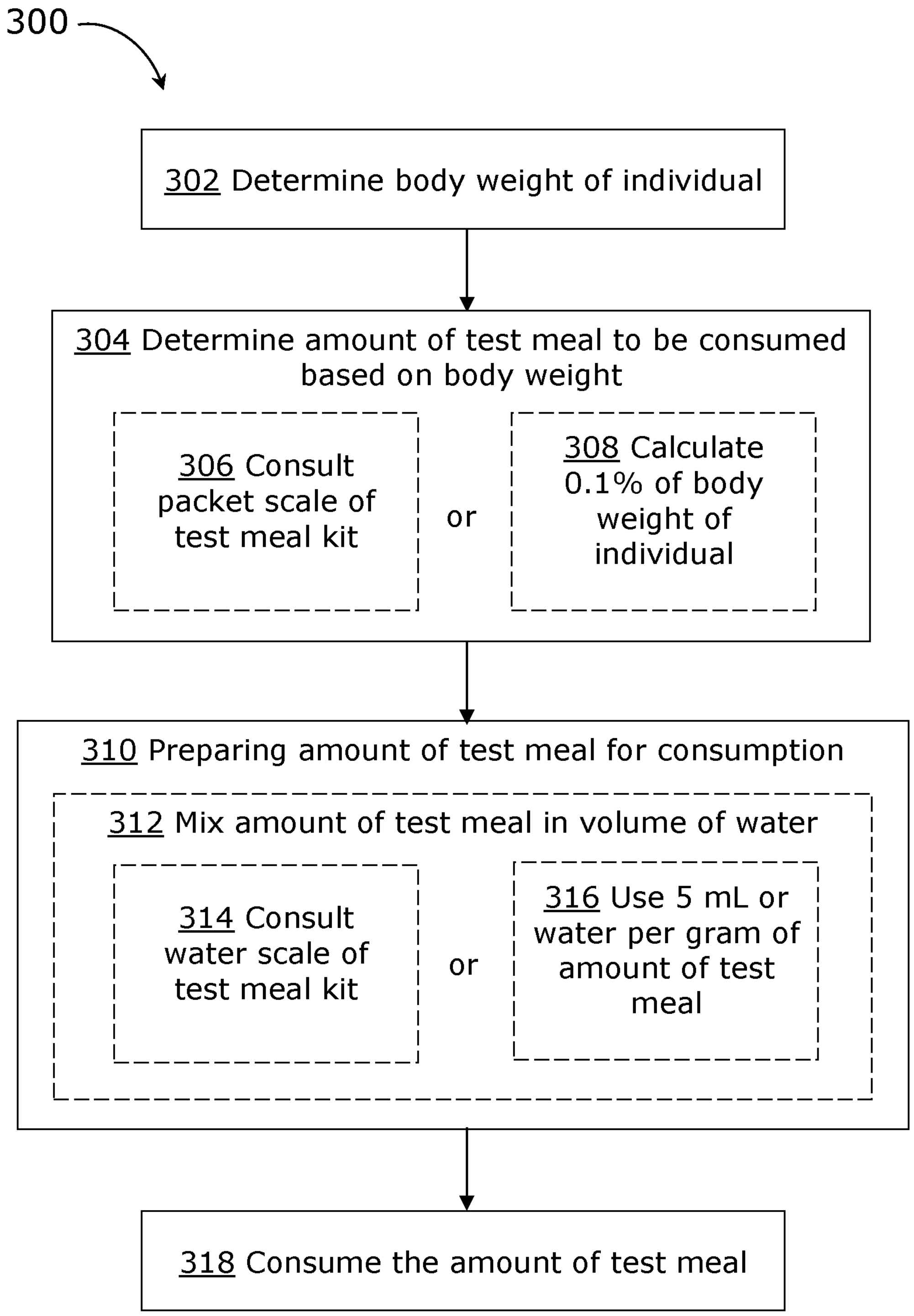
FIG. 3 is a flow chart illustrating a method of using test meal in the detection of prediabetes according to an embodiment of the present invention.

A method (300) of using test meal in the detection of prediabetes in an individual is illustrated in FIG. 3. In the present embodiment, the test meal used in method (300) is the test meal described above. In other embodiments, other test meals may be used. For example, a mixed meal with a range of doses such as Boost™ or Ensure™ would work as long as it was standardized according to body weight.

Any standardized mixed test meal with sufficient glucose content would work, so long as it had a sufficient amount of dextrose. The sugar content could be higher or lower as long as it produced a sufficiently high degree of hyperglycemia to allow quantification that could detect small changes. The MIG score (discussed below) will be different if the meal content of dextrose is different. For example, if a low dose of sugar was used, the MIG score might be so low that the difference between a healthy and prediabetic score may be minor. Increasing the amount of test meal will increase the degree of postprandial hyperglycemia.

At (302), the first step involves determining a body weight of the individual. Such a determination may be made by weighing the individual on a scale, or simply consulting a record previously made of the body weight of the individual.

To simplify calculations, the body weight of the individual may be rounded down to the nearest 5 to get a rounded body weight. The amount of the test meal to be consumed by the individual may then be determined relative to the rounded body weight of the individual.

At (304), the amount of the test meal to be consumed by the individual is to be determined, where the amount corresponds to the body weight of the individual. Optionally, at (306), determining the amount of test meal may simply involve using test meal kit (100) as described above, and consulting packet scale (102) to determine the number of first and second packets 12, 14 the individual is to consume that corresponds to the body weight of the individual.

Alternately, at (308), determining the amount of test meal may involve calculating the amount of test meal. In the present case, the amount of test meal is calculated to be 0.08%-0.1% of the body weight of the individual, and preferably, 0.1% of the body weight of the individual. Thus, if the body weight of the individual is 65 kg, the calculated amount of test meal is 65 g.

At (310), the amount of test meal is prepared for consumption by the individual. Since the present test meal is in powdered form, it is made more palatable by being mixed with water at (312).

Thus, optionally at (314), if test meal kit (100) is being used, water scale (104) may be consulted to determine the volume of water that the amount of test meal is to be mixed with depending on the body weight of the individual.

For example, if the individual has a body weight of 60 kg, pouch (106) may be filled with water until the internal water level reaches measurement marker/fill line (114) that corresponds with (i.e. immediately adjacent to) 60 kg. If the individual's body weight falls between two fill lines (114), such as 62 kg, the user may fill to the higher line corresponding to 65 kg. As noted above, pouch (106) is dimensioned such that when the fill line (114) corresponding to 60 kg, for example, is reached by the water, the amount of water within internal space (110) correspondingly 300 mL.

The amount of test meal from first and second packets 12, 14 may then be poured into the corresponding volume of water in pouch (106). The combination may be stirred, or resealable seal (118) may be closed and pouch (106) may be shaken to mix the contents therein.

Alternately, rather than using measurement markers 114, the user may independently measure the corresponding amount of water before pouring it into pouch (106).

If test meal kit (100) is not used, at (316), determining the volume of water may involve calculating and measuring the volume of water. In the present case, the volume of water is proportional to the weight of the amount of test meal, such as 5 mL of water per gram of the amount of test meal.

Once the corresponding volume of water is mixed with the determined amount of test meal, at (318), the individual consumes the amount of test meal shortly after the mixing, preferably within 5 minutes of the mixing.

Method of Diagnosing Prediabetes

Figure 4:
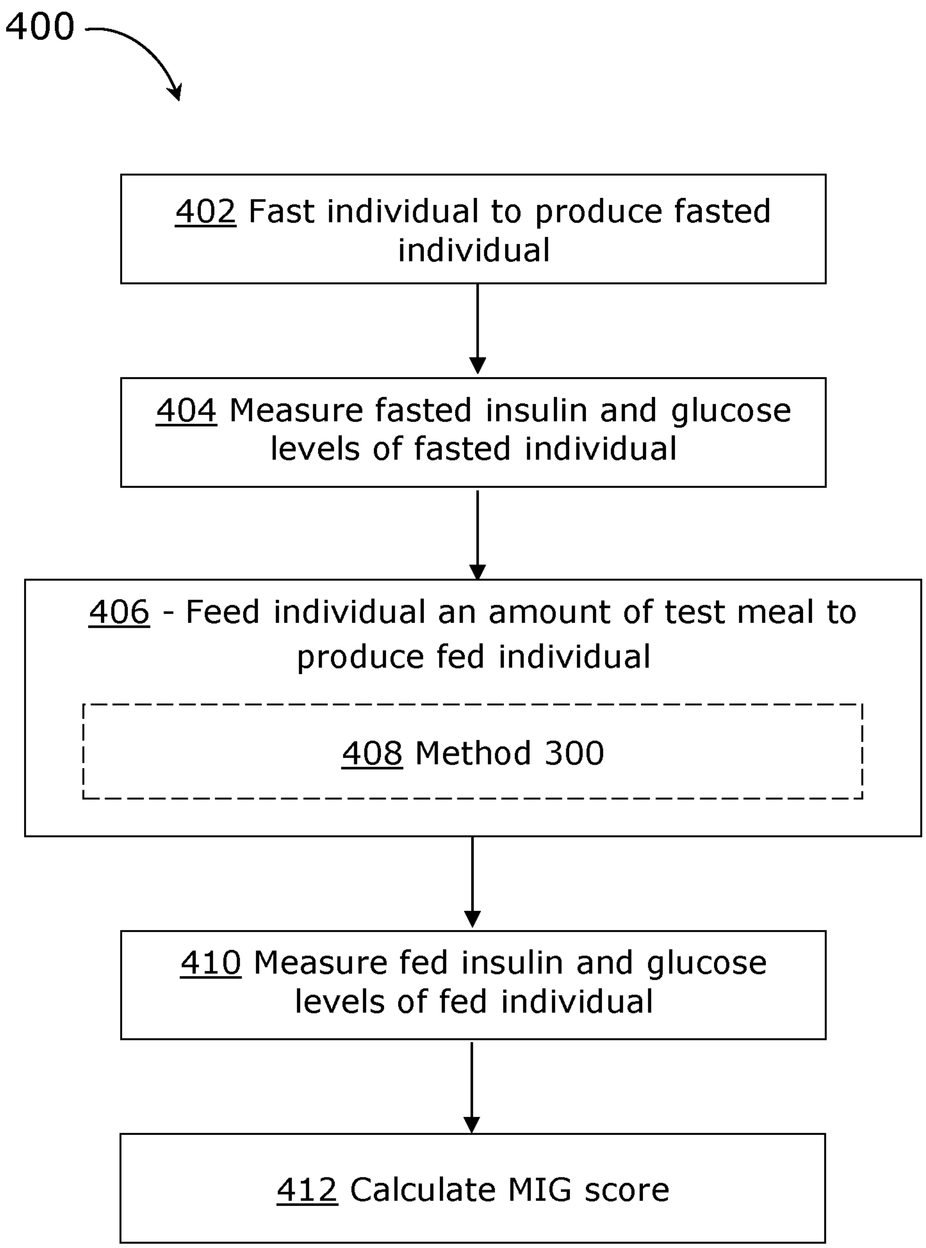
FIG. 4 is a flow chart illustrating a method of diagnosing prediabetes according to an embodiment of the present invention.

A method (400) of diagnosing prediabetes in an individual is illustrated in FIG. 4. In the present embodiment, the test meal used in method (400) is the test meal described above.

At (402), the individual fasts for a period of time to produce a fasted individual. For example, an approximate 12 hour fast may be sufficient.

The insulin and glucose levels of the fasted individual are then measured at (404) to get a fasted insulin level ($I_{fast}$) and a fasted glucose level ($G_{fast}$) of the individual. The fasted insulin and glucose levels of may be measured in a manner known in the art.

At (406), the individual is then fed an amount of test meal to produce a fed individual. In the present embodiment, at (408), the individual may be fed using method (300) as described above, where the amount of test meal fed to the individual is proportional to the body weight of the individual.

The insulin and glucose levels of the fed individual are then measured at (410) to get a fed insulin level ($I_{fed}$) and a fed glucose level ($G_{fed}$) of the individual. The fed insulin and glucose levels of may be measured in a manner known in the art, similar to the above. Preferably, measuring of the fed insulin level and the fed glucose level is performed 60-90 minutes after the feeding.

At (412), a meal induced insulinemia and glycemia (MIG) score is calculated by determining the differential between the insulin level and the glucose level of the fed individual and the insulin level and glucose level of the fasted individual.

In particular, the MIG score may be determined by the formula:

$$MIG=(I_{fed}\times G_{fed})-(I_{fast}\times G_{fast})$$

wherein $I_{fed}$ is the insulin level of the fed individual $G_{fed}$ is the glucose level of the fed individual $I_{fast}$ is the insulin level of the fasted individual $G_{fast}$ is the glucose level of the fasted individual.

The MIG score indicates the degree of Meal-induced Insulin Sensitization (MIS) in the individual. The lower the MIG score, the higher the degree of MIS in the individual, while the higher the MIG score, the lower the degree of MIS in the individual.

Method of Determining Diabetes Treatment Efficacy

Figure 5:
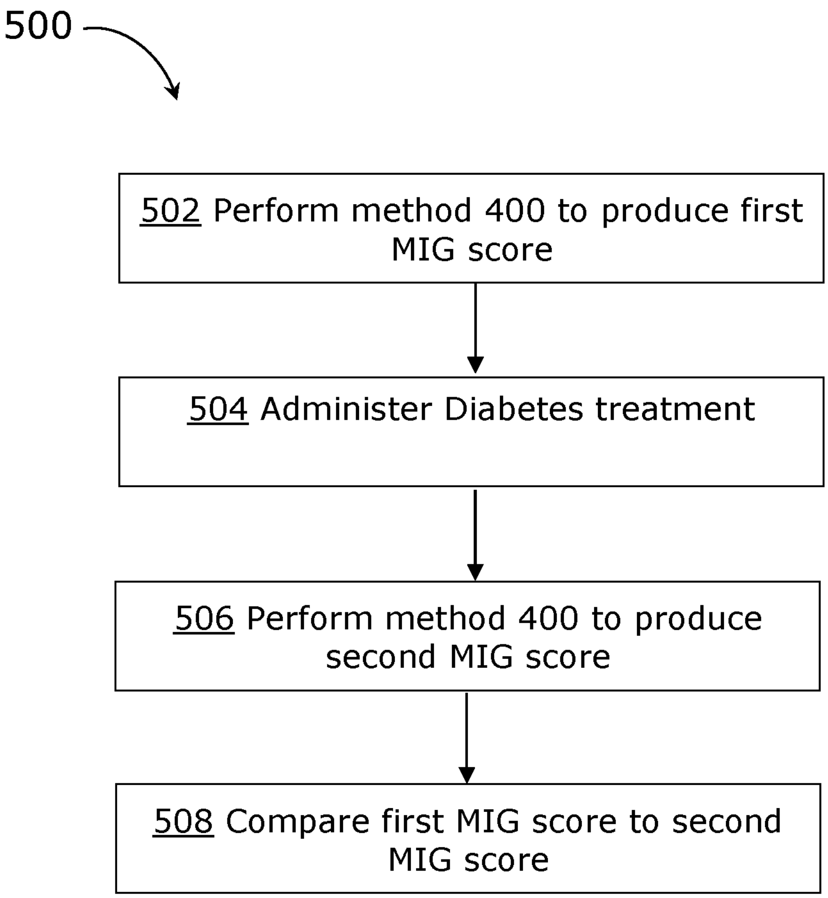
FIG. 5 is a flow chart illustrating a method of determining efficacy of a diabetes treatment according to an embodiment of the present invention.

A method (500) of determining the efficacy of a diabetes treatment in an individual is illustrated in FIG. 5. In the present embodiment, the test meal used in method (500) is the test meal described above. In other embodiments, other test meals may be used. Full activation of the ability of insulin to activate HISS secretion from the liver would occur with a wide range of mixed meals. However, the increase in levels of insulin, HISS and glucose elevation would depend on the composition of the meal, especially the glucose (dextrose) quantity. The MIG score is, however, unique for each test meal.

At (502), the diagnostic method (400) as described above is performed to produce a first MIG score ($MIG_1$).

At (504), the diabetes treatment under study is performed on the individual. For example, the diabetes treatment may be a drug that is administered to the individual.

At (506), the diagnostic method (400) as described above is performed again to produce a second MIG score ($MIG_2$)

At (508), the first MIG score is compared with the second MIG score. If the second MIG score is lower than the first MIG score ($MIG_1>MIG_2$), this indicates that the diabetes treatment is effective. If the second MIG score is the same or higher than the first MIG score ($MIG_1\leq MIG_2$), this indicates that the diabetes treatment is ineffective.

Alternately, rather than a diabetes treatment, the activity under study may be a diabetes lifestyle intervention performed by the individual. For example, the diabetes lifestyle intervention may be the regular performance of a particular type of exercise by the individual.

In such a case, method (500) may be performed in a similar manner where the diagnostic method (400) as described above is performed to produce a first MIG score ($MIG_1$). The diabetes lifestyle intervention may then be administered or performed by the individual. The diagnostic method (400) as described above is then performed again to produce a second MIG score ($MIG_2$), and the first MIG score is compared with the second MIG score. As before, if the second MIG score is lower than the first MIG score ($MIG_1>MIG_2$), this indicates that the diabetes lifestyle intervention is effective. If the second MIG score is the same or higher than the first MIG score ($MIG_1\leq MIG_2$), this indicates that the diabetes lifestyle intervention is ineffective.

Example 1—Animal Studies

The initiating defect in prediabetes is related to absence of the action of the hormone, HISS (Hepatic Insulin Sensitizing Substance) and results in reduced glucose uptake in skeletal muscle which normally would account for as much as 80% of total glucose uptake after a meal. Blood levels of glucose rise higher and for longer as extra insulin is secreted to compensate for absence of HISS action. Thus, absence of HISS action results in elevations of either or both glucose and insulin, depending on the scale from prediabetes to diabetes.

Ming et al (Ming Z, Legare D J and Lautt W W. 2009. Obesity, syndrome X and diabetes: the role of HISS-dependent insulin resistance altered by sucrose, an antioxidant cocktail and age. Can. J. Physiol. Pharmacol. 87: 873-882) showed HISS action and in postprandial nutrient processing comparing young 9 week old rats with aged rats (12 months) aged rats fed a 5% sucrose supplement in drinking water, and rats that had the sucrose supplement but also had treatment with SAMEC (S-adenosyl methionine (0.5 g/kg diet), vitamin C (12.5 g/kg diet) and vitamin E (1.5 g/kg diet)) in the chow.

Fed and fasting levels of insulin and glucose previously reported are used for the MIG calculation as an index of utility to quantify the degree of metabolic dysfunction on the progression from health to diabetes.

Figure 6:
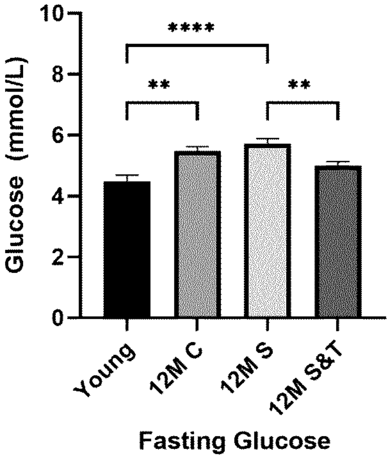
FIG. 6 is a graph showing levels of glucose in fasting rats.

Figures show the lowest MIG score in the young healthy rats and the highest score in the old rats on sucrose. Rats were fasted for 8 hours. FIG. 6 is a graph showing levels of glucose in fasting rats. Young rats are 9 weeks old. 12M rats are 52 weeks old, 12 months. C indicates the untreated controls. S indicates sucrose supplement. T indicates Treatment with SAMEC (S-adenosyl methionine plus vitamins C and E). S & T indicates Sucrose supplemented and treated with SAMEC.

Figure 7:
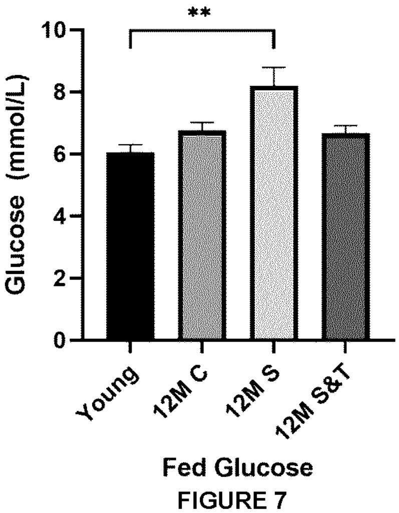
FIG. 7 is a graph showing levels of glucose in fed rats.
Figure 8:
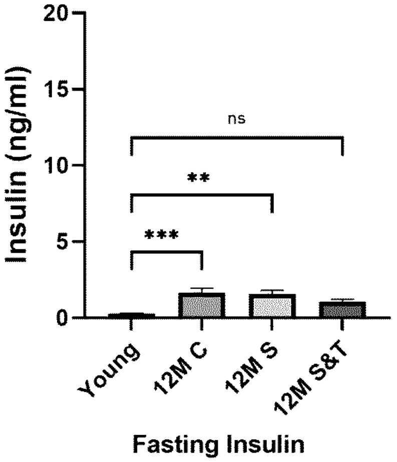
FIG. 8 is a graph showing levels of insulin in fasting rats
Figure 9:
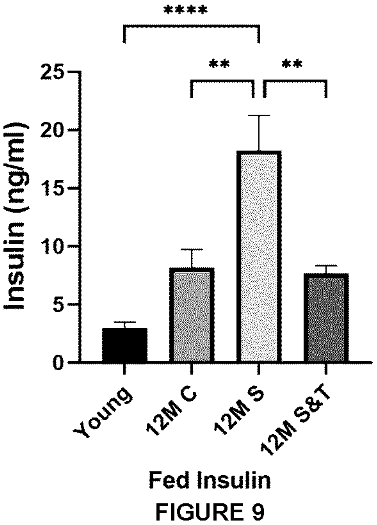
FIG. 9 is a graph showing levels of insulin in fed rats.
Figure 10:
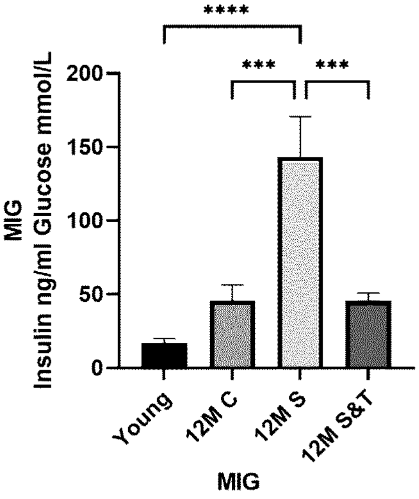
FIG. 10 is a graph showing calculated MIG in rats.

FIG. 7 is a graph showing levels of glucose in fed rats. FIG. 8 is a graph showing levels of insulin in fasting rats. FIG. 9 is a graph showing levels of insulin in fed rats. FIG. 10 is a graph showing calculated MIG in rats.

Of note, the SAMEC supplemented rats had complete protection against the detrimental effect of the sucrose with the MIG score being similar to the control aged group.

Example 2—Human Studies

For clinical use the MIG is meaningful only if a calibrated, standardized test meal is used. The NuPaTest meal, a reconstituted powdered mixed meal calibrated to body weight, was given to 5 young, fit healthy human volunteers after an overnight fast. Volunteers were fasted for 12 hours.

A fasting blood sample was taken and the liquid meal consumed and the postprandial sample was taken at 60 minutes.

Figure 11:
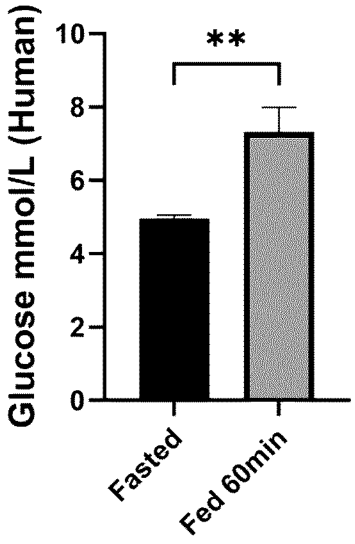
FIG. 11 is a graph showing glucose levels in fasted and fed humans.
Figure 12:
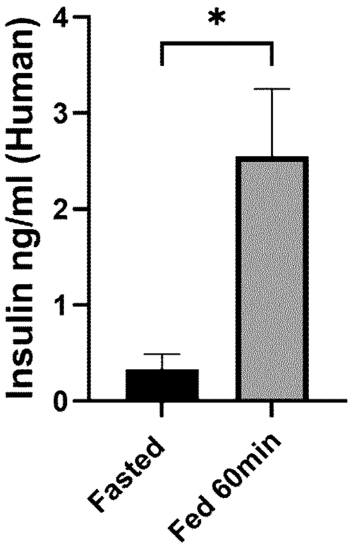
FIG. 12 is a graph showing insulin levels in fasted and fed in humans.
Figure 13:
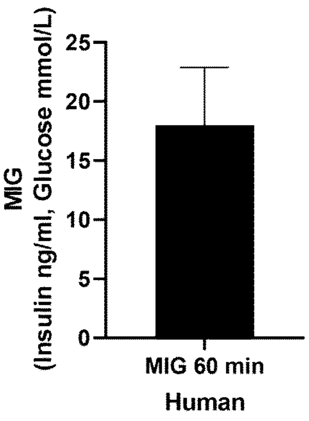
FIG. 13 is a graph showing calculated MIG in humans.

FIG. 11 is a graph showing glucose levels in fasted and fed humans. FIG. 12 is a graph showing insulin levels in fasted and fed in humans. FIG. 13 is a graph showing calculated MIG in humans. The MIG score for healthy lean young humans was 18.0 SE 4.9.

Although the invention has been described with reference to illustrative embodiments, it is understood that the invention is not limited to these precise embodiments and that various changes and modifications may be effected therein by one skilled in the art. All such changes and modifications are intended to be encompassed in the appended claims.

REFERENCES

Afonso et al., 2010 Br. J. Nutr. 104 1450-1459
Afonso et al. 2016 J. Nutr. Biochem. 27: 70-78.
Caperuto et al., 2008 Endocrinology 149(12): 6326-35
Chowdhury et al., 2011 Exp. Gerontol 46: 73-80 (202)
Fernandes et al., 2011 J. Neuroendocrinol. 23(12): 1288-1295
Grundy et al., 2005 Circulation 112 2735-2752 (pmid 16157765)
Lautt et al., 1998 Can. J. Physiol. Pharmacol. 76:1080-1086
Lautt et al., 2001 Am J Physiol. 281:G29-G36 (152)
Lautt et al., 2008 Exp. Gerontol. 43:790-800 (191)
Lautt et al., 2010 Can J Physiol. Pharmacol. 88:313-323. (195)
Lautt et al., 2011 Can. J. Physiol. Pharmacol. 89:135-142. (200)
Patarrao et al., 2008 Can. J. Physiol. Pharmacol. 86, 880-888. (192)
Porszasz et al., 2003 Br J Pharmacol. 139(6):1171-9 5
Ribeiro et al., 2005 Diabetologia 48: 976-983 (173)
Sadri et al., 2003 Can. J Diabetes 27:239-247 (164)
Sadri et al., 2006 Br. J. Nutr. 95:288-295 (179)
Seredycz et al., 2006 Neuroendocrinology 84:94-102 (183)
Xie et al., 2006 J Pharmacol. Toxicol. Meth. 35: 77-82 (116)

The invention claimed is:

1. A method of diagnosing prediabetes in an individual, the method comprising:

fasting the individual for a period of time to produce a fasted individual;

measuring a fasted insulin level and a fasted glucose level of the fasted individual;

feeding the individual an amount of test meal to produce a fed individual, the test meal comprising about 2% to about 8% by weight of lecithin;

measuring a fed insulin level and a fed glucose level of the fed individual;

calculating a meal induced insulinemia and glycemia score by determining the differential between the insulin level and the glucose level of the fed individual and the insulin level and glucose level of the fasted individual;

wherein the meal induced insulinemia and glycemia score indicates the degree of Meal-induced Insulin Sensitization in the individual.

2. The method of claim 1, wherein the meal induced insulinemia and glycemia score is determined by the formula:

$$\text{meal induced insulinemia and glycemia}=(I_{fed}\times G_{fed})-(I_{fast}\times G_{fast})$$

wherein $I_{fed}$ is the insulin level of the fed individual $G_{fed}$ is the glucose level of the fed individual $I_{fast}$ is the insulin level of the fasted individual $G_{fast}$ is the glucose level of the fasted individual.

3. The method of claim 2, wherein measuring of the fed insulin level and the fed glucose level is performed about 60 to about 90 minutes after the feeding.

4. The method of claim 2, wherein the amount of test meal fed to the individual is proportional to a body weight of the individual.

5. The method of claim 4, wherein the amount of test meal is about 0.08% to about 0.1% of the body weight of the individual.

6. The method of claim 2, wherein the test meal comprises dextrose, lecithin, and soy protein.

7. The method of claim 6, wherein the test meal comprises about 82.5% by weight of dextrose, about 5% by weight of lecithin, and about 12.5% by weight of soy protein.

8. The method of claim 2, wherein the amount of test meal is in powdered form, the method further comprising mixing the amount of test meal in a volume of water before consumption by the individual.

9. The method of claim 8, wherein the volume of water is about 5 mL of water for every gram of the amount of test meal.

10. A test meal composition for consumption by an individual based on a body weight of the individual for detection of prediabetes, the test meal composition comprising:

dextrose, lecithin, and soy protein;

the lecithin forming about 2% to about 8% by weight of the test meal composition.

11. The test meal composition of claim 10, wherein the composition comprises 80-85% by weight of dextrose.

12. The test meal composition of claim 10, wherein the composition comprises about 5% by weight of lecithin.

13. The test meal composition of claim 10, wherein the composition comprises about 10 to about 15% by weight of soy protein.

* * * * *